US008012728B2

(12) United States Patent
Metzner et al.

(10) Patent No.: US 8,012,728 B2
(45) Date of Patent: *Sep. 6, 2011

(54) THROMBIN PREPARATIONS AND PROCESS FOR THEIR PRODUCTION

(75) Inventors: Hubert Metzner, Marburg (DE); Heinrich Scheider, Lahntal (DE)

(73) Assignee: CSL Behring GmbH, Marburg (DE)

( * ) Notice: Subject to any disclaimer, the term of this patent is extended or adjusted under 35 U.S.C. 154(b) by 174 days.

This patent is subject to a terminal disclaimer.

(21) Appl. No.: 11/385,713

(22) Filed: Mar. 22, 2006

(65) Prior Publication Data

US 2006/0182735 A1 Aug. 17, 2006

Related U.S. Application Data

(62) Division of application No. 09/809,021, filed on Mar. 16, 2001, now Pat. No. 7,351,561.

(30) Foreign Application Priority Data

Mar. 18, 2000 (DE) ................................. 100 12 732

(51) Int. Cl.
*C12N 9/00* (2006.01)

(52) U.S. Cl. ....................................... 435/183

(58) Field of Classification Search ........................ None
See application file for complete search history.

(56) References Cited

U.S. PATENT DOCUMENTS

| | | | |
|---|---|---|---|
| 3,962,421 A | 6/1976 | Neurath | |
| 4,297,344 A | 10/1981 | Schwinn et al. | |
| 4,363,319 A | 12/1982 | Altshuler | |
| 4,409,334 A | 10/1983 | Lill et al. | |
| 4,540,573 A | 9/1985 | Neurath et al. | |
| 4,579,735 A | 4/1986 | Heimburger et al. | |
| 4,623,717 A | 11/1986 | Fernandes et al. | |
| 4,696,812 A | 9/1987 | Silbering et al. | |
| 4,876,241 A | 10/1989 | Feldman et al. | |
| 5,219,328 A | 6/1993 | Morse et al. | |
| 5,397,704 A | 3/1995 | Boctor et al. | |
| 5,723,123 A | 3/1998 | Karges et al. | |
| 5,866,122 A | 2/1999 | Turecek et al. | |
| 5,945,103 A | 8/1999 | Hanada et al. | |
| 6,013,620 A | 1/2000 | Turecek et al. | |
| 6,110,721 A * | 8/2000 | Gibbs et al. | ............ 435/214 |
| 6,358,534 B1 | 3/2002 | Schwarz et al. | |
| 6,777,390 B1 | 8/2004 | Matthiessen et al. | |
| 7,354,585 B2 * | 4/2008 | Adams et al. | ............ 424/145.1 |

FOREIGN PATENT DOCUMENTS

| | | |
|---|---|---|
| DE | 31 22 926 A1 | 7/1982 |
| DE | 195 31 637 | 3/1997 |
| DE | 198 53 033 A1 | 5/2000 |
| EP | 0 221 700 A2 | 5/1987 |
| EP | 0 302 754 A2 | 2/1989 |
| EP | 0 439 156 A1 | 7/1991 |
| EP | 0 444 692 A1 | 9/1991 |
| EP | 0 543 178 B1 | 5/1993 |
| EP | 0 796 623 | 9/1997 |
| JP | 56-39782 | 4/1981 |
| WO | WO 96/09376 | * 3/1996 |
| WO | WO 98/44942 | 10/1998 |
| WO | WO 99/00356 A1 | 1/1999 |
| WO | WO 99/37304 A1 | 7/1999 |
| WO | WO 99/66031 | 12/1999 |

OTHER PUBLICATIONS

O'Farrell, pp. 461-467, Molecular Biomethods Handbook, 1998.*
J. Hauptmann, "Pharmacokinectics of an Emerging New Class of Anticoagulant/Antlthrombic Drugs," *Eur. J. Clin. Pharmacol.*, 57: 751-758 (2002).
J. Sturzebecher et al., "Interactions of Thrombin with Benzamindine-based Inhibitors", *Biol. Chem. Hoppe-Seyler*, 373: 491-496 (1992).
J. L. Lorne et al., "Purification de la Thrombin Humaine par Chromotographie d'Affinite en Vue de son Utilisation dans les Preparations de Colle Biologique", *Rev. Fr. Transfus. Hemobiol.*, 32: 391-402 (1989).
M. Allary et al., "Isolement par Chromatographie d'Affinite, sur Support de Silice, de la Thromblne Humaine en Vue de son Utilisation dans les Preparations de Colle Biologique," *Ann. Pharmaceutiques Françaises*, 48(3): 129-135 (1990).
J. Chabbat et al., "Properties of a New Fibrin Glue Stable in Liquid State", *Thromb. Res.* 76: 525-533 (1994).
D. V. Brezniak et al., "High Stability of Dilute Human α-Thrombin in Salt Solutions", *Blood Coagulation and Fibrinolysis*. 5:847-848 (1994).
B. H. Landis et al., "Human Thrombins: Group 1A and IIA salt-Dependent properties of α-Thrombin," *The Journal of Biological Chemistry*, 256: 4604-4610 (1981).
J. W. Felton et al., "Human Thrombins: Production, Evaluation, and Properties of α-Thrombin," *The Journal of Biological Chemistry*, 252: 3587-3598 (1977).
K. Wilson and J. Walker, Eds., *Practical Biochemistry*, 4th Ed., New York, NY: Cambridge University Press, 1994, cover page and pages 491-492.
KG Mann, "Prothrombin and Thrombin," in Hemostasis and Thrombosis, 3rd Ed., 1994, pp. 184-199, R.W. Colman et al., Eds., J.B. Lippincott Co., Philadelphia, PA.
K.-O Eriksson, "Hydrophobic Interaction Chromatography," in "Protein Purification—Principles, High Resolution Methods," 1989, pp. 207-226, J.C. Jansen & L. Rydén, Eds., VCH Publishers, Inc.

* cited by examiner

*Primary Examiner* — Michael Meller
(74) *Attorney, Agent, or Firm* — Finnegan, Henderson, Farabow, Garrett & Dunner, L.L.P.

(57) ABSTRACT

The production of a thrombin preparation which is obtained from prothrombin which is, after activation to thrombin without the addition of thromboplastin, purified by a hydrophobic interaction chromatography, it being possible subsequently also to inactivate or remove viruses, is described. Before or after the hydrophobic interaction chromatography it is also possible in addition to carry out a cation exchange chromatography. A thrombin preparation which contains as stabilizer a noncovalently binding inhibitor and to which further stabilizers can be added for stabilization in the liquid state is additionally described.

10 Claims, No Drawings

THROMBIN PREPARATIONS AND PROCESS FOR THEIR PRODUCTION

This application is a division of application Ser. No. 09/809,021, filed Mar. 16, 2001, now U.S. Pat. No. 7,351,561 which claims priority to German Application No. DE 100 12 732.0, filed Mar. 18, 2000, both of which are incorporated herein by reference in their entirety.

The invention relates to a thrombin preparation which is stable in the liquid state and is distinguished by high purity and virus safety, and to a process for its production.

Since it became possible to produce thrombin commercially, several applications thereof have emerged. The main applications to be mentioned at present are, besides diagnostic purposes, the use as local hemostatic or as component of a tissue glue together with a fibrogen-containing component. The precondition for use of thrombin for medical purposes is that it can be made available to the clinician as a stable product which has high virus safety and contains minimal amounts of inactive byproducts or degradation products of thrombin or other factors.

Numerous methods for stabilizing thrombin have already been proposed. Thus, Japanese Patent Application No. 56-39782 discloses a process in which organic mono- or polycarboxylic acids and/or mono- or polyhydroxycarboxylic acids are employed to produce stable aqueous solutions of thrombin. Japanese Patent Application No. 57-18985 discloses albumin as thrombin stabilizer, and Japanese Patent Application No. 62-106028 discloses a buffer solution as stabilizer. European Patent Application 0 302 754 proposes a sugar and an amino acid, preferably in a concentration of from 1 to 10% by weight, as stabilizers for thrombin solutions.

German Published Specification 31 22 926 further discloses a storable thrombin preparation which, besides sodium chloride, makes use of polyhydric alcohols with 3 to 6 carbon atoms, sulfur-free amino acids and polyethylene glycol for producing thrombin solutions. Finally, European Patent Application 0 221 700 describes a thrombin preparation which is buffered at a pH of from 5 to 8 and may contain, where appropriate, sodium chloride and a polyhydroxy compound.

Buffered and stabilized thrombin solutions are also disclosed in a publication by J. Chabbat et al. [J. Chabbat, M. Tellier, P. Porte and M. Steinbuch; Properties of a new fibrin glue stable in liquid state, Thromb. Res. 76: 525-533 (1994)].

In addition, a publication by D. V. Brezniak, H. I. Hassouna and J. W. Fenton II [Blood Coagulation and Fibrinolysis, 6, 847-848 (1994)] has already described the effect of salts on the stability of dilute $\alpha$-thrombin solutions. It was shown in this study that sodium chloride concentrations of 0.3 mol/l and above have a marked stabilizing effect in dilute thrombin solutions. It is stated that thrombin is stable in sodium chloride-containing solutions at 37° C. for about 2 weeks, and thus the stability is greater than in calcium chloride-containing solutions, which may possibly be explained by better thermal stability in relation to denaturation.

Numerous patent applications have also described processes for producing high-purity thrombin preparations. Thus, European Patent Application 0 439 156 discloses a process for producing a purified thrombin with a specific activity of more than 1600 U/mg, which can be employed for hemostasis. This entails using thromboplastin to activate prothrombin and employing an anion exchange chromatography and a cation exchange chromatography with support materials based on agarose. An "ultra-pure", clear, colorless bovine thrombin with a specific activity of about 8000 to 11,000 NIH U/mg is described in U.S. Pat. No. 5,397,704. Thromboplastin from bovine lung is employed therein for prothrombin activation, and anion exchange chromatography and cation exchange chromatography are used for purification of the protein.

However, none of the processes disclosed to date allows a purified, calcium ion-containing, virus-safe thrombin preparation which is stable in the liquid state at 0° C. and higher temperatures, and whose thrombin activity after 12 months or more is still over 70-80% of the initial level, to be produced. The object therefore is to develop a process for producing such a thrombin preparation, the intention being to dispense with the use of thromboplastin for prothrombin activation for reasons of product safety. An additional object was to avoid high concentrations of polyols as added stabilizers, because this results in an unwanted increase in the viscosity of the preparation.

It has now been found that this object is achieved by a process for producing a thrombin preparation in which a prothrombin obtained from plasma or a plasma fraction is, after activation to thrombin without the addition of thromboplastin and, where appropriate, further processing steps, purified by a hydrophobic interaction chromatography and, where appropriate, subsequently the viruses are inactivated or removed.

A further improvement in this process is possible if a cation exchange chromatography is additionally carried out before or after the hydrophobic interaction chromatography. The chromatographies in this case may be carried out as "positive" (binding of the thrombin) or as "negative" (binding of the impurities) chromatography.

Since an adequate purity of the thrombin solution employed is necessary to achieve high thrombin stability in the liquid state, a simple and improved process was sought for using high-purity thrombin with high virus safety. It is possible to use as basis for example the process described in European Patent Application 0 543 178 for producing a thrombin concentrate. However, other processes in which partially purified prothrombin is activated to thrombin in the presence of calcium salts can also be employed according to the invention as starting material for producing the thrombin preparation.

If hydrophobic interaction chromatography (HIC) is employed alone or in combination with a cation exchange chromatography (CEC) for purifying thrombin, then effective and simple purification is achieved thereby. The sequence of these two chromatography processes is moreover as desired. If the chromatography is carried out initially with a hydrophobic support, the thrombin eluate can then be bound directly to the cation exchanger and eluted therefrom with a salt gradient. Combination of these two separation principles results in a thrombin preparation of high purity in a good yield of about 70% over the two purification steps. This simultaneously achieves good removal of byproducts such as activated or unactivated coagulation factors and of thrombin forms having little or no activity in the coagulation test (e.g. prothrombin, $\beta$-thrombin, $\gamma$-thrombin or other thrombin or prothrombin fragments). Combination of the two chromatography processes mentioned results in higher purity than use of ion exchange chromatography on its own.

The production process of the invention is carried out in such a way that initially thrombin of low or moderate purity is produced. This can take place by adsorbing prothrombin from plasma or a plasma fraction on an ion exchanger. The prothrombin obtained in this way can then be subjected to a virus inactivation, e.g. by pasteurization or another known method, and, where appropriate, further processing steps, and then the thrombin can be activated by processes known per se without the addition of thromboplastin obtained from animal tissue. The subsequent hydrophobic interaction chromatography then reduces the concentration of concomitant plasma proteins, activated factors or their fragments, and of thrombin degradation products. This purification effect is further enhanced by the subsequent cation exchange chromatography.

Elution of pure thrombin is followed by addition of suitable buffer substances to adjust the pH of the preparation to the range from 5 to 8, and stabilizers are added. It is also possible to add buffer substance(s) and stabilizers together.

The adsorbent employed in the hydrophobic interaction chromatography, which is known per se as chromatographic method, is a gel with coupled hydrophobic radicals. Particularly suitable hydrophobic radicals are in this case phenyl radicals or other ligands with a similar hydrophobicity. The cation exchanger preferably employed is a gel with high resolution for the various thrombin variants. Examples of suitable cation exchange gels are Fractogel EMD $SO_3$ (Merck, Darmstadt), Macro Prep 50S (Biorad, Munich) or other cation exchangers complying with requirements in relation to purification and sterilizability.

The thrombin solution obtained after chromatographic purification can then be subjected directly to virus inactivation or virus reduction such as, for example, filtration through small-pore membranes, which makes it possible effectively to remove even the smallest viruses while obtaining a high yield of thrombin. Virus inactivation or reduction can, however, also take place before the chromatographic purification of thrombin if this facilitates the overall process (e.g. through removal of unwanted components or byproducts in the subsequent chromatography).

For formulation of the thrombin preparation as a component, which is stable and storable in the liquid and, where appropriate, also in the frozen state, for use in a tissue glue or on its own as local hemostatic, a buffer should be used to adjust to a pH of about 5.0 to 8.0. To achieve the desired effect on use and for stabilization, then a soluble calcium salt, sodium chloride, a sugar or a pure alcohol and/or an amino acid or else the salt of a mono- or polycarboxylic acid and/or the salt of a mono- or polyhydroxycarboxylic acid is added to the preparation. This results in good stabilities in the liquid and/or frozen state for a storage time of 12 months and more.

It has also emerged that addition of substances which inhibit noncovalently the thrombin activity in vitro can seemingly only increase the stability even further, especially at room temperature, by diminishing the autolysis of thrombin. Suitable substances for this purpose are compounds such as benzamidine or p-aminobenzamidine or other low to moderate affinity protease inhibitors. Addition of these low or moderate affinity inhibitors negligibly impairs the activity of thrombin in relation to substances such as fibrinogen, and thus also, for example, the later use as component of a tissue glue.

It is possible via the process of the invention to produce thrombin preparations which can be stored in the liquid and/or frozen state for months or years and whose activity does not fall below 70-80% in this period.

It is possible with the process of the invention to produce, even in the presence of calcium salts which reduce the thermal stability of thrombins [B. H. Landis, K. A. Koehler and J. W. Fenton II; Human Thrombins. J Biol chem 256: 4604-4610 (1981)], thrombin preparations which result in high stability at 4° C. for up to 24 months and more, as can be demonstrated in the coagulation test. Many of the thrombin preparations shown in Table 4 are also stable in the frozen state and, in most cases, show stability at room temperature for a period of 3 to 6 months. The stability at room temperature can be increased in particular by adding low or moderate affinity thrombin inhibitors such as, for example, benzamidine, p-aminobenzamidine or other protease or thrombin inhibitors, without this involving a significant decrease in the activity in relation to fibrinogen in the coagulation test.

The thrombin preparations produced by the described process can be employed inter alia as components of a fibrin glue which can be stored in the liquid or frozen state and consists of two components, e.g. of a thrombin-containing component and of a fibrinogen-containing component, or consisting of three components, e.g. of a thrombin-containing component, fibrinogen-containing component and factor XIII-containing component, as described inter alia in German Patent Application 198 53 033.1. It is moreover possible either for the thrombin preparation produced in this way to be mixed in situ with the other components, or, in the case of a three-component fibrin glue, for it to be mixed beforehand with one of the components before the third component is added. However, it is also possible to produce, lyophilized thrombin preparations using the process of the invention for therapeutic purposes, in which case a correspondingly high stability is observed in the liquid state after reconstitution.

Finally, the thrombin concentrates produced according to the invention can also be employed alone or in combination with carrier materials as agent for local stoppage of bleeding.

The process of the invention is explained in more detail by the following examples:

EXAMPLE 1

Thrombin Purification

Starting from a thrombin concentrate of low or moderate purity, produced by known processes, two chromatography steps were carried out.

Initially the thrombin solution was mixed with 0.6 mol/l sodium sulfate and adsorbed onto a hydrophobic interaction chromatography (HIC) gel (in this case: Phenyl-Sepharose HP, manufacturer: Amersham Pharmacia, Freiburg, Germany) which had previously been equilibrated with buffer A (10 mmol/l Na phosphate pH 6.5) containing 0.6 mol/l sodium sulfate. After washing with buffer A containing 0.6 mol/l sodium sulfate, the bound thrombin was eluted by a gradient with decreasing sodium sulfate content in buffer A. Impurities and thrombin fragments were to a large extent removed in the flow-through or in the wash fractions.

The thrombin fraction was loaded without further treatment directly onto a cation exchange column (CEC; in this case: FRACTOGEL® EMD SO3, manufacturer: Merck, Darmstadt, Germany) equilibrated with buffer A, washed with equilibration buffer A and eluted by a gradient from 0 to 1.0 mol/l sodium chloride in buffer A. During the separation, final byproducts and thrombin fragments were removed so that the resulting α-thrombin eluate had a high specific purity of about 3500 IU/mg (protein determination by determining the absorption at 280 nm and using the conversion factor of 1.74 for a 0.1% strength solution in accordance with J. W. Fenton, II, M. J. Fasco, A. B. Stackrow, D. L. Aronson, A. M. Young and J. S. Finlayson, Human Thrombins. J Biol Chem 252; 3587-3598 (1977)). Table 1 shows the results of this thrombin purification and the resulting specific activity.

At this stage, the thrombin can be stored in a chilled or deep-frozen state until processed further.

TABLE 1

| Sample | Absorption 280 nm | Protein* (mg/ml) | Activity [IU/ml] | Specific activity (I U/mg) |
|---|---|---|---|---|
| Thrombin, starting material | 13.78 | 7.92 | 6418 | 810 |
| HIC eluate | 1.085 | 0.624 | 1372 | 2199 |
| CEO eluate | 6.65 | 3.822 | 13370 | 3498 |

*$A_{280, 0.1\%} = 1.74$

EXAMPLE 2

Thrombin Purification

Starting from a thrombin concentrate of moderate or low purity, two chromatography steps were carried out. Initially the thrombin solution was mixed with 0.6 mol/l sodium sulfate and adsorbed onto a hydrophobic interaction chromatography (HIC) gel (in this case: Phenyl-Sepharose HP, manufacturer: Amersham Pharmacia, Freiburg, Germany) which had previously been equilibrated with buffer B (10 mmol/l Na phosphate 0.1% PEG pH 6.5; (in this case PEG 6000, but other molecular weight ranges can also be employed)) containing 0.6 mol/l sodium sulfate. After washing with buffer B containing 0.6 mol/l sodium sulfate, the bound thrombin was eluted by a gradient with decreasing sodium sulfate content in buffer B. Impurities and thrombin fragments were to a large extent removed in the flow-through or in the wash fractions.

The thrombin fraction was loaded without further treatment directly onto a cation exchange column (CEC; in this case: FRACTOGEL® EMD SO3, manufacturer: Merck, Darmstadt, Germany) equilibrated with buffer C (10 mmol/l Na phosphate, 166 mmol/l L-arginine pH 6.5), washed with equilibration buffer C and eluted by a gradient from 0 to 1.0 mol/l sodium chloride in buffer C. During the separation, final byproducts and thrombin fragments were removed so that the resulting α-thrombin eluate had a high specific purity of about 3300 IU/mg (cf. Table 2).

At this stage, the thrombin obtained can be stored in a chilled or deep-frozen state until processed further.

TABLE 2

| Sample | Absorption 280 nm | Protein* (mg/ml) | Activity [IU/ml] | Specific activity (IU/mg) |
|---|---|---|---|---|
| Thrombin, starting material | 12.49 | 7.178 | 5895 | 821 |
| HIC eluate | 2.042 | 1.174 | 2696 | 2296 |
| CEC eluate | 8.03 | 4.615 | 15,150 | 3283 |

*$A_{280, 0.1\%} = 1.74$

EXAMPLE 3

Thrombin Purification

A thrombin purification was carried out as in Example 1 but with the difference that the buffer employed for the chromatography contains 20 mmol/l L-histidine in place of sodium phosphate. The results of purification with this modification are comparable to Example 1, but further processing to the final product may be simplified if in this case, for example, histidine is to be present as buffer substance.

EXAMPLE 4

Thrombin Purification and Filtration

Starting from a thrombin eluate purified as in Examples 1 to 3 and after hydrophobic interaction chromatography and cation exchange chromatography, a filtration was carried out on a membrane with a small pore size (e.g. PLANOVA™ 15 nm). Even small viruses such as parvoviruses can be effectively removed with this membrane. It was found that on use of the purified thrombin as starting material, very good yields in terms of thrombin activity and protein were obtained, with a good filtration rate (see Table 3). This process is therefore suitable for producing a thrombin concentrate with high virus reduction factors.

TABLE 3

Filtration of 123 ml of purified thrombin through a Planova ™ 15 nm module (0.001 m²)

| Sample | Thrombin activity, total | Protein, total* |
|---|---|---|
| Before filtration | 800,240 IU | 245.3 mg |
| After filtration | 797,960 IU | 239.0 mg |
| Yield | 99.7% | 97.4% |

*$A_{280, 0.1\%} = 1.74$

EXAMPLE 5

Thrombin Formulations

Starting from thrombin purified by chromatography, various formulations were produced and stored at temperatures of −20° C., 4° C., 20-25° C. and, in some cases, also at 37° C. These thrombin solutions were produced by diafiltration of the purified thrombin concentrates against the formulation buffer or by diafiltration against a basic buffer and adding the remaining additives, adjusting the pH and adjusting the thrombin concentration. Thrombin concentrations of about 1 to about 15,000 IU/ml can be produced in this way.

The stability of the formulations was tested by determining the thrombin activity in a coagulation test with fibrinogen as substrate. Table 4 shows a selection of the formulations of the invention and their stabilizer composition, and Table 5 shows the corresponding stability data at up to three temperatures.

TABLE 4

Composition of thrombin formulations 1. 360 mmol/l NaCl, 40 mmol/l CaCl₂, 5 mmol/l L-histidine ph 6.0
2. 360 mmol/l NaCl, 40 mmol/l CaCl₂, 2% (w/v) mannitol, 5 mmol/l L-histidine pH 6.0
3. 150 mmol/l NaCl, 40 mmol/l CaCl₂, 2% (w/v) mannitol, 5 mmol/l L-histidine pH 6.0
4. 90 mmol/l NaCl, 40 mmol/l CaCl₂, 100 mmol/l Na succinate, 5 mmol/l L-histidine pH 6.0
5. 90 mmol/l NaCl, 40 mmol/l CaCl₂, 100 mmol/l Na succinate, 2% (w/v) mannitol, 5 mmol/l L-histidine pH 6.0
6. 150 mmol/l NaCl, 40 mmol/l CaCl₂, 100 mmol/l Na succinate, 5 mmol/l L-histidine pH 6.0

TABLE 4-continued

Composition of thrombin formulations 7. 90 mmol/l NaCl, 40 mmol/l CaCl$_2$, 50 mmol/l Na lactate, 2% (w/v) mannitol, 5 mmol/l L-histidine pH 6.0
8. 90 mmol/l NaCl, 40 mmol/l CaCl$_2$, 2% (w/v) mannitol, 10 mmol/l p-aminobenzamidine, 5 mmol/l L-histidine pH 6.0
9. 90 mmol/l NaCl, 40 mmol/l CaCl$_2$, 2% (w/v) mannitol, 10 mmol benzamidine, 5 mmol/l L-histidine pH 6.0
10. 90 mmol/l NaCl, 40 mmol/l CaCl$_2$, 4% (w/v) HSA, 5 mmol/l L-histidine pH 6.0
11. 90 mmol/l NaCl, 40 mmol/l CaCl$_2$, 1% (w/v) mannitol, 142 mmol/l L-arginine, 5 mmol/l L-histidine pH 6.0
12. 90 mmol/l NaCl, 40 mmol/l CaCl2, 100 mmol/l Na succinate, 0.1% polyvinylpyrrolidone (K15), 5 mmol/l L-histidine pH 6.0.

TABLE 5

Stability of thrombin in various formulations at 4° C., −20° C., 20-25° C.,

| Storage time (month) | \multicolumn{12}{c}{Mixture} | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| \multicolumn{13}{c}{Thrombin activity (% of baseline value), storage temperature: 4° C.} |
| 0 | 100 | 100 | 100 | 100 | 100 | 100 | 100 | 100 | 100 | 100 | 100 | 100 |
| 1 | 101.5 | 95.8 | 98.9 | 94.0 | 100.4 | 100.8 | 110.6 | 102 | 98.0 | 106.8 | 108.3 | 98.0 |
| 3 | 98.9 | 109.8 | 103.4 | 103.1 | 108.8 | 104.5 | 101.6 | 95.6 | 91.5 | 98.5 | 102.3 | 103.9 |
| 6 | 100.5 | 117.5 | 88.4 | 97.3 | 99.0 | 98.2 | 108.1 | 97.6 | 95.2 | 103.0 | 99.4 | 101.9 |
| 9 | 97.5 | 112.9 | 95.6 | 94.2 | 91.9 | 91.6 | 122.7 | 102.2 | 99.6 | 102.2 | 91.5 | 108.0 |
| 12 | 100.2 | 116.5 | 93.6 | 92.4 | 105.8 | 106.4 | 117.2 | 100.2 | 97.8 | 101.2 | 93.5 | 103.8 |
| 18 | 89.7 | 101.7 | — | 94.7 | | | 112.7 | — | — | 89.2 | 95.8 | 104.1 |
| 24 | 100.5 | | 86.8 | 95.5 | | | | 100 | | 94.3 | 89.2 | 96.2 |
| \multicolumn{13}{c}{Thrombin activity (% of baseline value), storage temperature: −20° C.} |
| 0 | 100 | | 100 | 100 | 100 | 100 | | | 100 | 100 | 100 | |
| 1 | 103.6 | | 100.4 | 88.6 | 94.3 | 94.9 | | | 47.1 | 111.0 | 106.5 | |
| 3 | 97.5 | | 92.6 | 104.2 | 93.0 | 93.9 | | | 91.5 | 103.0 | 101.3 | |
| 6 | 99.5 | | 92.7 | 101.3 | 99.7 | 98.2 | | | 68.6 | 107.3 | 96.4 | |
| 9 | 100.3 | | 81.3 | 92.9 | 89.2 | 87.6 | | | 92.1 | 108.0 | 95.3 | |
| 12 | 94.3 | | 100.5 | 95.3 | 104.4 | 98.5 | | | 79.2 | 104.0 | 95.1 | |
| 18 | 94.3 | | — | 92.7 | | | | | — | 99.3 | 99.8 | |
| 24 | 99.0 | | 90.7 | 100.7 | | | | | 97.2 | 104.2 | 100.2 | |
| \multicolumn{13}{c}{Thrombin activity (% of baseline value), storage temperature: 20-25° C.} |
| 0 | 100 | 100 | 100 | 100 | 100 | 100 | 100 | 100 | 100 | 100 | 100 | 100 |
| 1 | 105.6 | 92.4 | 90.9 | 91.8 | 92.6 | 94.3 | 95.5 | 101.7 | 99.8 | 107.3 | 99.4 | 81.1 |
| 3 | 92.3 | 88.2 | 86.9 | 88.4 | 80.0 | 77.9 | 75.8 | 95.4 | 96.3 | 84.2 | 98.9 | 77.0 |
| 6 | 85.6 | 66.3 | 66.8 | 80.4 | 71.4 | 68.6 | 75.3 | 92.8 | 89.0 | 69.4 | 84.8 | 60.6 |
| 9 | 72.1 | 58.3 | 58.8 | 75.9 | 51.8 | 50.7 | 59.1 | 96.1 | 91.9 | 48.8 | 74.4 | 53.3 |
| 12 | 64.2 | 50.1 | 51.5 | 65.3 | 43.7 | 43.9 | 42.8 | 100.9 | 90.6 | 42.9 | 64.7 | 46.6 |
| 18 | | | | | | | | — | — | | | |
| 24 | | | | | | | | 90.1 | 82.4 | | | |

We claim:

1. A process for producing a thrombin preparation, which comprises obtaining prothrombin from plasma or a plasma fraction, performing ion exchange chromatography on the prothrombin, activating the prothrombin to thrombin, performing hydrophobic interaction chromatography on the activated thrombin, and performing cation exchange chromatography on the hydrophobic interaction chromatography eluate to yield said thrombin preparation, wherein the hydrophobic interaction chromatography eluate is bound directly to the cation exchange chromatography medium and eluted with a salt gradient, and wherein the yield of thrombin in the thrombin preparation is at least about 70%.

2. The process as claimed in claim 1, wherein the prothrombin is subjected to virus inactivation or reduction during its production.

3. The process as claimed in claim 1, wherein the thrombin is subjected to an inactivation or reduction of viruses, before or after the hydrophobic interaction chromatography.

4. The process as claimed in claim 1, wherein the thrombin preparation is adjusted to a pH of from 5.0 to 8.0.

5. The process as claimed in claim 1, wherein the thrombin preparation comprises a soluble calcium salt, a sodium chloride as stabilizer, a buffer substance, and at least one of a sugar, a sugar alcohol, an amino acid, a salt of a mono- or polycarboxylic acid, or a salt of a mono- or polyhydroxycarboxylic acid.

6. The process as claimed in claim 1, wherein a noncovalently binding inhibitor of thrombin activity is added as stabilizer.

7. The process as claimed in claim 6, wherein the noncovalently binding inhibitor of thrombin activity is benzamidine or p-aminobenzamidine.

8. The process as claimed in claim 1, wherein a gel with coupled hydrophobic radicals is employed as absorbent for the hydrophobic interaction chromatography.

9. The process as claimed in claim 8, wherein the hydrophobic radicals are phenyl radicals.

10. The process as claimed in claim 1, further comprising filtering the thrombin preparation through a membrane with a suitable pore size to remove viruses.

* * * * *

UNITED STATES PATENT AND TRADEMARK OFFICE
CERTIFICATE OF CORRECTION

| | | |
|---|---|---|
| PATENT NO. | : 8,012,728 B2 | Page 1 of 1 |
| APPLICATION NO. | : 11/385713 | |
| DATED | : September 6, 2011 | |
| INVENTOR(S) | : Metzner et al. | |

It is certified that error appears in the above-identified patent and that said Letters Patent is hereby corrected as shown below:

Title Page, Item (75), Inventors, the second inventor's last name should read --Schneider-- not "Scheider".

Signed and Sealed this
Twenty-sixth Day of June, 2012

David J. Kappos
*Director of the United States Patent and Trademark Office*